United States Patent [19]

Scheibl

[11] Patent Number: 4,724,136
[45] Date of Patent: Feb. 9, 1988

[54] PREPARATIONS, MAINLY CONFECTIONERY PREPARATIONS REDUCING THE INCIDENCE OF DENTAL CARIES AND METHODS OF PREPARING SAID PREPARATIONS

[75] Inventor: Jozsef Scheibl, Csaszartoltes, Hungary

[73] Assignee: Konsumex Kulkereskedelmi Vallalat, Budapest, Hungary

[21] Appl. No.: 809,557

[22] Filed: Dec. 16, 1985

[51] Int. Cl.$^4$ .......................... A61K 7/16; A61K 9/68; A61K 9/20; A61K 9/28
[52] U.S. Cl. ........................................ 424/50; 424/93; 426/62; 426/805
[58] Field of Search ................... 426/62, 805; 424/50, 424/93, 94

[56] References Cited

U.S. PATENT DOCUMENTS

| | | | |
|---|---|---|---|
| 1,386,252 | 8/1921 | Green | 424/50 |
| 2,154,168 | 4/1939 | Klein et al. | 424/50 |
| 3,194,738 | 7/1965 | Harrisson et al. | 424/50 |
| 4,162,336 | 7/1979 | Brown et al. | 426/805 |
| 4,265,913 | 5/1981 | Eichelburg | 426/805 |
| 4,554,154 | 11/1985 | White | 424/151 |

FOREIGN PATENT DOCUMENTS 53-127842 11/1978 Japan ........................... 424/50

*Primary Examiner*—Ronald W. Griffin
*Attorney, Agent, or Firm*—Karl F. Ross; Herbert Dubno; Jonathan Myers

[57] ABSTRACT

The invention relates to preparations, mainly confectionery preparations reducing the incidence of dental caries and to methods of preparing said preparations. The preparation contains a mixture of yeast and mono- and disacharides and polysacharide preferably in an amount corresponding at least to the partial ratio of mono- or disacharides, optionally further components conventionally used in confectionery products in the form of solid or liquid edible product.

8 Claims, No Drawings

PREPARATIONS, MAINLY CONFECTIONERY PREPARATIONS REDUCING THE INCIDENCE OF DENTAL CARIES AND METHODS OF PREPARING SAID PREPARATIONS

The invention relates to preparations, mainly confectionery preparations reducing the incidence of dental caries and to methods of preparing said preparations.

Dental caries is widely recognized as being caused by acids, e.g. lactic acid generated by the decomposition of the remains of food, mainly carbohydrates which adhere to the surface of teeth. Said acids dissolve dental enamel, generating thus a hollow, resulting in further dental disease. In order to prevent dental caries, the limited consumption of carbohydrates, such as sweets or pastry for children or adults or mouth care following each meal is generally suggested. On the basis of today's medical-biological knowledge the immediate dental or mouth care daily or several times a day after every meal cannot be realized. Inspite of regular dental and mouth care the complete removal of the plaque from the openings between the teeth or which adhere to the surface of teeth cannot be fully solved inspite of various cleaning devices.

The present invention is aimed at a preparation, mainly confectionery preparation reducing the incidence of dental caries without showing the above disadvantages.

The preparation of the invention can be characterized by a content of polysacharides added to the mixture of yeast, mono- and disacharides, preferably at an amount corresponding at least to the partial ratio of mono- or disacharides. As polysaccharide starch-, cellulose-, inuline, pentosan-, dextran-containing materials, such as whole wheat flour, rye flour, barley flour, oat flour, maize flour, soyabean flour or a grist of seeds or tubers of other plants, ground peanut, cocoa, soyabeans, or dried flour of Jerusalem artichoke, hip, fruit or vegetables or a powder, liquid concentrate, extract or a mixture thereof can be used.

Fruit and vegetable arts are chosen so as to contain Vitamins A, C. It is an important feature of the invention that related to the total amount of the composition 7–50% by mass mono- or disacharides and preferably an equivalent amount of polysacharide and optionally further components used in confectionery preparations are admixted to 5–10% by mass of yeast, and the mixture is converted at room temperature to a confectionery product of solid, pulpy, plastic or liquid consistence.

From the mixture of yeast, mono-, disacharides and polysacharides a confectionery product is obtained which is suitable for fermentation in the mouth. As such products chewable capsules, tablets, chewing gums, extruded maize, dragées, nougat, wafer biscuits, crémes, parfait, ice-cream or pudding may be mentioned.

The preparation according to the invention is dissolved in the saliva and if the composition contains yeast fungus grains, they will be dissolved, revived, will grow, propagate utilizing the sugar remaining on the mucous membrane in the mouth, on the teeth as well as the introduced polysacharide decomposing same to alcohol and carbon dioxide.

The preparation of the invention purifies the mouth "consuming" the carbohydrates, proteins and lipids of the residual plaque in the tooth holes or orifices formed by the bacteria. It decreases the total bacterium number and simultaneously the number of bacteria which decompose sugars into lactic acid.

In the composition of the invention yeast fungus can be used in dried state. One may also proceed by admixing yeast extract with the above carriers at an appropriate ratio. According to the invention the following Saccharomyces strains belonging to Saccharomyces cerevisiae deposited in public depositories can preferably be used: NCTC 467, NRRL Y-129, NCTC 1809, NRRL Y-44, NRRL 4-138, NRRL Y-139, NRRL Y-145, NCTC 06, NCTC 4614, NCTC 79, NRRL Y-973, NRRL Y-635, NRRL Y-529, NRRL Y-633.

It is preferred not to use a composition containing an isolated, purified, "single" strain as it is too expensive for utilization, but to use a mixture of several strains i.e. baker's yeast, ale or wine yeast prepared in the practice for other purposes. The simple "baker's yeast" available in shops can be used paricularly preferably.

The use of desinfectants becomes unnecessary, as these desinfectants not only kill the harmful microorganisms but the useful, such as living, zymotic microorganisms too decreasing thus the tooth protecting effect.

Daily consumption of the new product in the form of 1 capsule, 1 tablet, 1 chewing gum, or 5–10 g dragee or candy decreases the acidic medium in the plaque, the effect being multiplied by several use or taking or consuming the above sweets. The upper limit is 4–5 capsules, tablets, chewing gum or 50–100 g dragee or candy a day, a higher dose does not increase the tooth protecting activity but cause windiness. Consumption of the above sweets decreases the destructing effect of sugar, protects teeth and they can be used in the wide range of popular, often used sweets, leading thus to good results.

The flour of wholly ground seeds contain the germ and bran of the seeds, thus by using the new preparation materials otherwise absent from our daily meals get into the organism and which harmonize the whole metabolism apart from the tooth protecting activity.

The breath improving effect appears a few hours after the consumption and becomes steady later.

The yeast present in the plaque ferments the residual sugars to alcohol and carbon dioxide. The plaque is diluted and dissolved by the formed alcohol and due to the function of the mimiking muscles the mouth (tongue, teeth) are purified biologically with the formed saliva. This effect is increased by carbon dioxide released in the form of little gas bubbles, loosening the plaque from the teeth.

The composition can further be used for the treatment of some skin diseases (acne-furunculosis) and it favorably influences some intestinal diseases due to its cellulose content. The yeast component contains the the following Vitamins: $B_1$ (thiamine), $B_2$ (lactoflavine), $B_3$, $B_4$, $B_5$, $B_6$ (pyridoxin), $B_7$, $B_{r'}$, $B_x$, p-amino-benzoic acid, nicotinic acid, pantothenic acid, hemogen, folic acid, factor anti tropical anaemia, Vitamin D and its provitamins, Vitamin E, Vitamin H (biotin), Vitamin T (exitatin), inosit, Vitamin K, Vitamin U. Vitamin A from flour of carrots and Vitamin C from hip flour, from whole corn flour, mineral materials, trace elements and further vitamins can be taken into the organism. Thus all known vitamins get naturally in traces into the organism continously, harmonizing thereby the growth of the children and keeping in balance the carbohydrate, lipid and protein metabolism of adults apart from the tooth protecting effect.

When a concentrated sugar solution spreads on the surface of teeth for 2 minutes, an osmotic pressure of about 28–52 atm appears on the surface of the teeth. The pressure inside of the teeth is corresponding to the osmotic blood pressure 6.8 atm. A liquid flow is generated due to the high osmotic pressure difference of the dental enamel through the semipermeable film in order to compensate the low and high pressure. The direction of the flow is reversed upon the consumption of the sugar of the saliva. The liquid flow caused by the osmotic pressure difference results in ion migration changing in centripetal or centrifugal direction.

Mineralization and demineralization relations of the teeth are changed by the ion migration when taking each sugar capsule, showing a cariogenic effect. This cariogenic effect generated by the sugar content of the capsule acts against the anti-caries alcoholic-fermenting activity of the yeast. The caries reducing activity is decreased by 25%, resulting altogether in a 40-60% caries reduction when using the yeast-sugar mixture.

Our invention can eliminate this 25% decrease of caries reducing effect by admixing wholly ground corn flour, vegetable powder etc. to the composition instead of sugar, carbohydrates of whole wheat flour are gradually decomposed by the ptialin of saliva (amylase) while eating and this is further decomposed in statu nascendi to alcohol and carbondioxide by the present yeast.

Further details of the invention are illustrated by the following Examples.

EXAMPLE 1

Filling of gelatin capsule:

cacao powder: 0.12 g
sorbitol: 0.06 g
dried yeast: 0.06 g
whole wheat flour: 0.12 g The mixture can be supplemented with flavoring and coloring agents and filled into colored gelatin capsules.

EXAMPLE 2

Tablet-like composition whole wheat flour: 0.30 g
sacharum album: 0.18 g
dried yeast: 0.06 g
citric acid: 0.002 g
talcum: 0.0005 g
magnesium stearate: 0.0005 g The mixture can be supplemented with flavoring and coloring agents and fed to tabletting machines.

EXAMPLE 3 extruded maize flour: 85.0 g
dried yeast: 7.0 g
sacharum album: 7.0 g
color agent: 1.0 g 800–1000μ particles of the endosperm part of maize are placed into an extruder where the grains are expanded. Maize starch expands at high temperature and under high pressure and gets swollen to 15 fold volume. The above mixture of yeast, sugar, flavoring and coloring agents are pressed through the extruder of chosen pattern.

EXAMPLE 4

Chewing gum:

spheric chewing-gum corpus: 2.66 g
dried yeast: 0.17 g
whole wheat flour: 0.33 g
sacharum album: 0.17 g Onto the spheric chewing gum the above amount of mixture of dried yeast-sugar-wheat flour-coloring-flavoring agent is applied by method known per se.

EXAMPLE 5

Raisin dragée:

raisin: 0.1 g
dried yeast: 0.1 g
whole wheat flour: 0.2 g
chocolate (cocoa): 0.8 g 50–100 kg of the above mixture are admixed in the above ratio and dragées weighing 2.0 g are prepared.

EXAMPLE 6

Wafer's biscuit:

wheat flour in wafer-sheet form: 20 g
butter: 20 g
sugar: 20 g
dried yeast: 3 g
citric acid: 0.5 g The filling is filled into a wafer-sheet by method known per se.

EXAMPLE 7

Nougat bar:

ground roasted peanut + chocolate: 40 g
sugar: 7.5 g
dried yeast: 2.5 g

Bars of 5 dkg are made and packed by the known technology.

I claim:

1. An orally administered dental composition for cleaning the teeth which is fermentable in the mouth to form alcohol and carbon dioxide from all saccharides present, to protect the teeth against dental caries, which consists essentially of:
    (a) 5 to 20% by weight of dried yeast;
    (b) 7 to 50% by weight of a monosaccharide or a disaccharide; and
    (c) 7 to 50% by weight of a polysaccharide; wherein the dried yeast ferments all saccharides present into alcohol and carbon dioxide thereby preventing conversion of the saccharides into lactic acid.

2. The composition defined in claim 1 wherein the dried yeast belongs to the Saccharomyces strain.

3. The composition defined in claim 1 wherein the polysaccharide is starch, cellulose, inulin, pentosan, or a dextran-containing material.

4. The composition defined in claim 1 wherein the polysaccharide is whole wheat flour, barley flour, rye flour, oat flour, maize flour, soybean flour, a grist of the seeds or tubers of other plants, ground peanut, cocoa, soya, or dried fruit of Jerusalem artichoke, hip, fruit or vegetables or a mixture thereof.

5. The composition defined in claim 4 in the form of a confectionery product.

6. The composition defined in claim 1 in the form of chewable capsules, tablets, dragees, chewing gum, extruded maize, nougat, wafer, parfait or pudding.

7. The composition defined in claim 1 wherein the disaccharide is not sugar.

8. A method of protecting the teeth against dental caries in children or adults in need of said treatment which comprises the steps of:
 (a) orally administering to said children or adults a therapeutically effective amount of an orally administered dental composition for cleaning the teeth which is fermentable in the mouth to form carbon dioxide and alcohol, which consists essentially of:
  (i) 5 to 20% by weight of dried yeast;
  (ii) 7 to 50% by weight of a monosaccharide or a disaccharide; and
  (iii) 7 to 50% by weight of a polysaccharide; and
 (b) allowing the dried yeast to ferment all saccharides present in the mouth into alcohol and carbon dioxide thereby preventing conversion of said saccharides into lactic acid.

* * * * *